US012780773B2

(12) United States Patent
Mamilla

(10) Patent No.: US 12,780,773 B2
(45) Date of Patent: Nov. 3, 2026

(54) METHOD FOR REACTIVE METHYL ACETATE DISTILLATION

(71) Applicant: SipChem Sahara International Petrochemical Company JSC, Al-Khobar (SA)

(72) Inventor: Sekhar Babu Mamilla, Al-Khobar (SA)

(73) Assignee: SipChem Sahara International Petrochemical Company JSC, Al-Khobar (SA)

( * ) Notice: Subject to any disclaimer, the term of this patent is extended or adjusted under 35 U.S.C. 154(b) by 426 days.

(21) Appl. No.: 18/640,539

(22) Filed: Apr. 19, 2024

(65) Prior Publication Data

US 2025/0326707 A1 Oct. 23, 2025

(51) Int. Cl.
*C07C 67/08* (2006.01)
*C07C 67/54* (2006.01)

(52) U.S. Cl.
CPC .............. *C07C 67/08* (2013.01); *C07C 67/54* (2013.01)

(58) Field of Classification Search
CPC ................................ C07C 67/08; C07C 67/54
See application file for complete search history.

(56) References Cited

U.S. PATENT DOCUMENTS 5,296,630 A 3/1994 Erpenbach et al.
6,028,215 A * 2/2000 Bessling ................ C07C 67/08 560/265
9,353,042 B2 5/2016 Perinet et al.

FOREIGN PATENT DOCUMENTS

CN 101328119 B 3/2011
CN 109503409 A 3/2019

OTHER PUBLICATIONS

Huss et al. ; Reactive distillation for methyl acetate production ; Computers and Chemical Engineering 27 ; Jun. 12, 2003 ; 12 Pages.
Mekala et al. ; Kinetics of esterification of methanol and acetic acid with mineral homogeneous acid catalyst ; Chinese Journal of Chemical Engineering 23 ; Nov. 13, 2014 ; 6 Pages.

* cited by examiner

*Primary Examiner* — Sikarl A Witherspoon
(74) *Attorney, Agent, or Firm* — Oblon, McClelland, Maier & Neustadt, L.L.P.

(57) ABSTRACT

A method for making methyl acetate from methanol and acetic acid in the presence of a catalyst added portion wise includes simultaneously introducing the acetic acid in the form of a liquid to an upper section of a reactive distillation column and the methanol in the form of a saturated stream at its boing point or as a vapor to a lower section of the reactive distillation column; contacting the acetic acid and the methanol in countercurrent flow in the body section of the reactive distillation column, and introducing at least a portion of the catalyst in the form of a liquid via at least two catalyst feed stream inlets thereby reacting the acetic acid and the methanol in the presence of the catalyst to form the methyl acetate in the form of a vapor.

20 Claims, 5 Drawing Sheets

Simple reactive distillation

METHOD FOR REACTIVE METHYL ACETATE DISTILLATION

BACKGROUND OF THE INVENTION

Technical Field

The present disclosure is directed to a method for making methyl acetate, particularly to a reactive distillation method for making methyl acetate from methanol and acetic acid in the presence of a catalyst added portion wise.

Description of the Related Prior Art

The description of the related prior art provided herein is for the purpose of generally presenting the context of the disclosure. Work of the presently named inventors, to the extent described in this background section, as well as aspects of the description which may not otherwise qualify as prior art at the time of filing, are neither expressly nor impliedly admitted as prior art against the present invention.

Reactive distillation (RD) is an approach that combines chemical reactions and distillation within a single multifunctional process unit. This process not only transcends the constraints imposed by chemical equilibrium but also empowers engineers and chemists to enhance selectivity and/or productivity while harnessing the heat generated by the reactions to facilitate in-situ distillation. The integration of chemical reactions and distillation within a single system offers possibilities for the chemical processing industry by overcoming the limitations of chemical equilibrium, enhancing product selectivity an/or yield, improving energy efficiency, and simplifying the design of chemical processes.

Methyl acetate is a fatty acid ester known for its low toxicity and excellent solubility. When used as an industrial solvent, methyl acetate finds applications in the realm of active pharmaceutical ingredient (API) synthesis and purification, adhesive manufacturing, cleaning solutions, nail polish removers, paper coatings, and the creation of synthetic fragrances and flavors.

The production of methyl acetate involves the esterification of methanol and acetic acid. This transformation occurs by substituting the hydroxyl group in the acetic acid with a methoxy group from the methanol. Typically, this esterification is facilitated by the presence of a catalyst, often a strong acid. In a distillative or partially gas phase process, when down coming acetic acid reacts with methanol vapor in the presence of an acid catalyst, e.g., sulfuric acid, to form methyl acetate, heat is released due to exothermic nature of the reaction. This heat has a noticeable impact on the temperature within the reaction column. The temperature profile of the column shows this sharp rise in temperature caused by the exothermic reaction, as depicted in FIG. 4. This sharp rise in temperature can often result in distillation column corrosion leading to equipment damage, unplanned shutdowns, and production losses. To combat the corrosion issue, the column and its internals are often built with advanced and expensive material of construction, e.g., hastelloy, zirconium etc. To further optimize the production process and enhance the yield of the desired product, water generated during the reaction may also be continuously removed. This helps maintain the reaction conditions at an optimal level and promotes the production of methyl acetate with increased efficiency.

CN109503409A discloses a method for separating DMF and making methyl acetate from methanol and acetic acid-containing DMF in the presence of sulfuric acid. The method includes reacting acetic acid-containing DMF with methanol in the presence of sulfuric acid in a rectifying tower with the acetic acid-containing DMF, the methanol and the sulfuric acid are each injected through the different injection points to form the methyl acetate. However, CN109503409A does not describe (i) portion wise addition of sulfuric acid as the reaction progresses over time, and (ii) a flattened temperature profile of the reaction.

U.S. Pat. No. 5,296,630A discloses a process for producing methyl acetate from acetic acid and methanol in the presence of a catalyst. The process includes reacting acetic acid with methanol in the presence of sulfuric acid at a temperature of 40 to 60° C. to form anhydrous methyl acetate in a distillation column. However, U.S. Pat. No. 5,296,630A does not describe (i) portion wise addition of sulfuric acid as the reaction progresses over time, and (ii) a flattened temperate profile of the reaction of making methyl acetate from acetic acid and methanol.

CN101328119B discloses a process for producing methyl acetate from acetic acid and methanol in the presence of a catalyst. The process includes reacting acetic acid with methanol in the presence of sulfuric acid to form the methyl acetate in a reaction rectification tower. However, CN101328119B does not describe (i) portion wise addition of sulfuric acid as the reaction progresses over time, and (ii) a flattened temperate profile of the reaction of making methyl acetate from acetic acid and methanol.

U.S. Pat. No. 9,353,042B2 discloses a process for producing methyl acetate from acetic acid and methanol in the presence of a catalyst. The process includes reacting acetic acid with methanol in the presence of sulfuric acid to form the methyl acetate in a packed bed reactor or a plug flow reactor. However, U.S. Pat. No. 9,353,042B2 does not describe (i) portion wise addition of sulfuric acid as the reaction progresses over time, and (ii) a flattened temperate profile of the reaction of making methyl acetate from acetic acid and methanol.

Huss et al. (*Comput Chem Eng.,* 2003) discloses a design of a reactive distillation column, and its application in methyl acetate production from acetic acid and methanol in the presence of a catalyst. The prior art reference describes acetic acid and methanol are reacted in liquid phase to form the methyl acetate in the presence of sulfuric acid. However, the prior art reference does not describe (i) portion wise addition of sulfuric acid as the reaction progresses over time, and (ii) a flattened temperate profile of the reaction of making methyl acetate from acetic acid and methanol.

Mekala et al. (*Chin. J. Chem. Eng.,* 2003) discloses a process for making methyl acetate from acetic acid and methanol in the presence of a catalyst in a batch stirred reactor. The prior art reference discloses that an increase of temperature and catalyst concentration will increase the reaction rate. However, the prior art reference does not describe (i) portion wise addition of sulfuric acid as the reaction progresses over time, and (ii) a flattened temperate profile of the reaction of making methyl acetate from acetic acid and methanol.

Reactive distillation has been used in the production of methyl acetate. However, the reaction of making methyl acetate from acetic acid and methanol in the presence of strong acid catalyst often suffers from high corrosion issue due to a temperature bump created by the exothermic reaction. The drawbacks of each of the methods described above indicate that there is still a need for effective and efficient temperature and/or reaction control to mitigate these challenges and ensure a methyl acetate production process with enhanced yield and minimized corrosion. More importantly, the challenge is that such methods should be cost-effective and rapid to attract industries to adopt these processes.

In view of the foregoing, one objective of the present disclosure is to provide a method for making methyl acetate from methanol and acetic acid in the presence of a strong acid catalyst added portion wise.

SUMMARY

In an exemplary embodiment, a method for making methyl acetate from methanol and acetic acid in the presence of a strong catalyst like sulfuric acid is added portion wise. The method includes simultaneously introducing the acetic acid in the form of a liquid to an upper section of a reactive distillation column via a first reactant feed stream inlet and the methanol in the form of a saturated stream at its bubble point to a lower section of the reactive distillation column via a second reactant feed stream inlet. In some embodiments, the reactive distillation column is in the form of a vertical cylindrical vessel containing the upper section, the lower section, and a body section between the upper section and the lower section with various diameters to accommodate the vapor and liquid flow that are specified in the standard distillation column design. In some embodiments, the upper section is in fluid communication with the lower section via the body section. In some embodiments, the upper section of the reactive distillation column includes a rectification section and an extractive distillation section. In some embodiments, the rectification section includes a product stream outlet. In some embodiments, the extractive distillation section includes the first reactant feed stream inlet, and a first plurality of catalyst feed stream inlets. In some embodiments, the body section of the reactive distillation column includes a second plurality of catalyst feed stream inlets. In some embodiments, the lower section of the reactive distillation column includes the second reactant feed stream inlet, a bottom stream outlet, and a reboiler vapor stream inlet. The method for making methyl acetate further includes contacting the acetic acid and the methanol in countercurrent flow in the body section of the reactive distillation column, and introducing at least a portion of the catalyst in the form of a liquid via at least two catalyst feed stream inlets thereby reacting the acetic acid and the methanol in the presence of the catalyst to form the methyl acetate in the form of a vapor and water. Additionally, the method for making methyl acetate includes removing the methyl acetate from the upper section of the reactive distillation column via the product stream outlet, and removing water and an excess amount of methanol from the bottom stream outlet.

In some embodiments, the catalyst is at least one acid selected from the group consisting of sulfuric acid, phosphoric acid, hydrochloric acid, p-toluenesulfonic acid, and methanesulfonic acid.

In some embodiments, the catalyst is sulfuric acid.

In some embodiments, the bottom stream outlet is in fluid communication with a boiler unit via a by-product pump, and wherein a reboiler vapor stream is introduced into the reactive distillation column via the reboiler vapor stream inlet.

In some embodiments, the first plurality of catalyst feed stream inlets are evenly spaced apart and disposed along the length direction of the reactive distillation column.

In some embodiments, each of the first plurality of catalyst feed stream inlets are in different planes along the length direction of the reactive distillation column.

In some embodiments, the first plurality of catalyst feed stream inlets are located on an outer sidewall of the extractive distillation section of the reactive distillation column.

In some embodiments, the second plurality of catalyst feed stream inlets are evenly spaced apart and disposed along the length direction of the body section.

In some embodiments, each of the second plurality of catalyst feed stream inlets are in different planes along the length direction of the reactive distillation column.

In some embodiments, the second plurality of catalyst feed stream inlets are located on an outer sidewall of the body section of the reactive distillation column.

In some embodiments, each of the at least two catalyst feed stream inlets are independently selected from the group consisting of the first plurality of catalyst feed stream inlets and the second plurality of catalyst feed stream inlets.

In some embodiments, each of the at least a portion of the catalyst are introduced at the same flow rate via the at least two catalyst feed stream inlets.

In some embodiments, the methanol and the acetic acid react in the presence of the catalyst, at an uppermost point of the body section of the reactive distillation column, to form the methyl acetate at a temperature $T_1$. In some embodiments, temperatures in the body section below the uppermost point of the reactive distillation column are higher than $T_1$. In some embodiments, a temperature in the lower section is higher than $T_1$.

In some embodiments, a temperature in the body section of the reactive distillation column from the uppermost point of the body section to a bottommost portion of the body section is within the range of $T_1$ to $T_1$+30° C.

In some embodiments, the catalyst is introduced portion wise via each of the at least two catalyst feed stream inlets as the reaction progresses over time, resulting in a flattened temperature profile of the reaction of making methyl acetate from acetic acid and methanol.

In some embodiments, a combined amount of the catalyst introduced portion wise is no more than an amount of the catalyst required in a method of making a same amount of methyl acetate from methanol and acetic acid with the catalyst added at a single catalyst feed stream inlet.

In some embodiments, the method for making methyl acetate has a production rate increased by 20 to 30% compared to a method of making methyl acetate from methanol and acetic acid with the catalyst added at a single catalyst feed stream inlet.

In some embodiments, the methyl acetate formed by contacting the acetic acid and the methanol is at least about 95% pure determined by gas chromatography (GC).

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
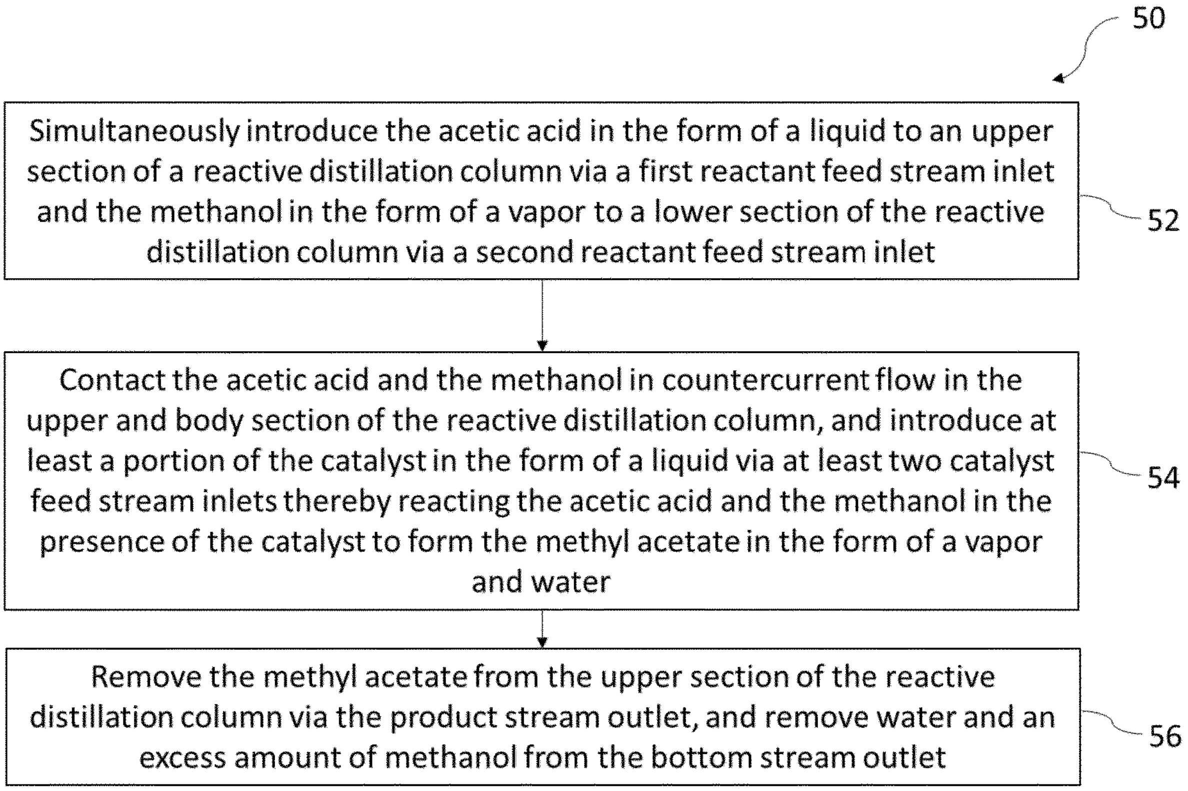
FIG. 1 is a flowchart depicting a method for making methyl acetate from methanol and acetic acid in the presence of a catalyst added portion wise, according to certain embodiments.

When describing the present disclosure, the terms used are to be construed in accordance with the following definitions, unless a context dictates otherwise. Embodiments of the present invention will now be described more fully hereinafter with reference to the accompanying drawings wherever applicable, in which some, but not all embodiments of the disclosure are shown.

In the drawings, like reference numerals designate identical or corresponding parts throughout the several views. Further, as used herein, the words "a," "an" and the like generally carry a meaning of "one or more," unless stated otherwise.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

The use of the terms "include," "includes", "including," "have," "has," or "having" should be generally understood as open-ended and non-limiting unless specifically stated otherwise.

The term "compounds" as used herein, refers to include the compounds disclosed in the present invention disclosure, salts, solvates, and salts of solvates, and mixtures, known and unknown variations and forms thereof.

One objective of the present disclosure is to describe a process that utilizes reactive distillation in the production of methyl acetate. The reactive distillation process of the present disclosure involves adding the catalyst, e.g., a strong acid, in multiple feeds with controllable, variable and/or reduced flow rates. The combined catalyst feed rate of the present disclosure may be equal or less in comparison to the feed rate of a conventional catalyst single feed process.

Figure 2:
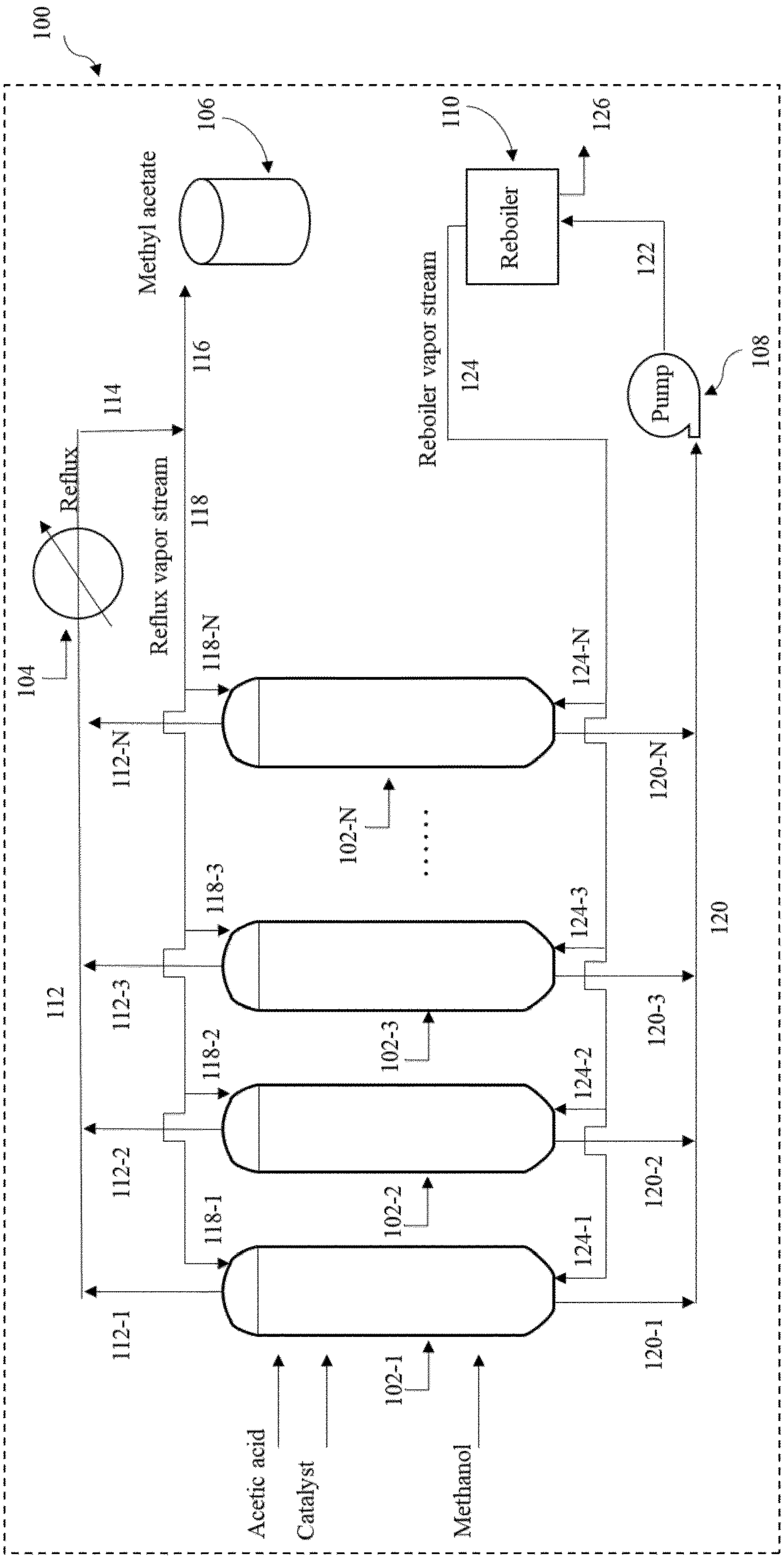
FIG. 2 is a schematic diagram illustrating a reactive distillation system used to carry out the methyl acetate production process, according to certain embodiments.

Referring to FIG. 2, illustrated is a schematic diagram of a reactive distillation system used to carry out the methyl acetate production process, represented by reference numeral 100 and hereinafter sometimes referred to as "system 100" or "integrated system 100" without any limitations. As illustrated, the reactive distillation system 100 includes one or more reactive distillation columns (as represented by reference numeral 102-1, 102-2, 102-3, and 102-N). In the present embodiments, the reactive distillation column 102-1 has at least two catalyst feed stream inlets (as discussed later in more detail and depicted in FIG. 3). Such a reactive distillation system may reduce temperature variations such as temperature bumps in temperature profile of the column, and provides an enhanced production rate of methyl acetate. In some embodiments, the multiple reactive distillation columns are arranged substantially parallel, and hereinafter sometimes referred to as "parallel-multistage reactive distillation columns". The basic working chemical reaction of the parallel-multistage reactive distillation columns 102 remains same as a single reactive distillation column but is carried out in systems with additional components, such as multiple reactant feed stream inlets (as discussed later and depicted in FIG. 3), multiple catalyst feed stream inlets (as discussed later and depicted in FIG. 3), multiple product stream outlets (as represented by reference numeral 112-1, 112-2, 112-3, and 112-N), multiple reflux vapor stream inlets (as represented by reference numeral 118-1, 118-2, 118-3, and 118-N), multiple bottom stream outlets (as represented by reference numeral 120-1, 120-2, 120-3, and 120-N), and multiple reboiler vapor stream inlets (as represented by reference numeral 124-1, 124-2, 124-3, and 124-N), to achieve advantageous column temperature profiles. In some embodiments, N is a positive integer. In some preferred embodiments, N is 2 to 20, preferably 3 to 18, preferably 4 to 16, preferably 5 to 14, preferably 6 to 12, or even more preferably 8 to 10. Other ranges are also possible.

The reactive distillation system 100 further includes a refluxing unit (as represented by reference numeral 104) and a methyl acetate storage tank unit (as represented by reference numeral 106). In the present embodiments, the refluxing unit 104 may be effective at removing dissolved gases, removing moisture, and/or removing impurities from the methyl acetate. In some embodiments, each of the multiple product stream outlets (112-1, 112-2, 112-3, and 112-N) are combined into a single product stream outlet 112 before entering the refluxing unit 104. The flow rate of each of the multiple product stream outlets (112-1, 112-2, 112-3, and 112-N) is independently controlled. In some embodiments, a refluxed stream 114, formed by passing the single product stream outlet 112 through the refluxing unit 104, may be divided into two streams, including a reflux vapor stream 118, and a methyl acetate stream 116. In some embodiments, the refluxing unit 104 is in fluid communication with the methyl acetate storage tank unit 106 via the methyl acetate stream 116. In some embodiments, the reflux vapor stream 118 may be fed back into the parallel-multistage reactive distillation columns if required. In some embodiments, the reflux vapor stream 118 may be divided into multiple reflux vapor stream inlets (118-1, 118-2, 118-3, and 118-N) before entering each of the corresponding reactive distillation column. The flow rate of each of the multiple product stream outlets (118-1, 118-2, 118-3, and 118-N) may be independently controlled. For example, the methyl acetate will be collected in a liquid form in the methyl acetate storage tank unit 106, and the reflux vapor stream containing the rest of the composition from steam 112 may be re-introduced into the reactive distillation columns. This first recirculating loop including the single product stream outlet 112, the refluxed stream 114, and the reflux vapor stream 118, the refluxing unit and the reactive distillation columns can be shared across multiple tanks that have different input and output requirements as a means of minimizing equipment size and cost.

Also referring to FIG. 2, the reactive distillation system 100 further optionally includes a by-product pump (as represented by reference numeral 108) and a reboiler (as represented by reference numeral 110). The by-product pump 108 is in fluid communication with each of the reactive distillation columns (102-1, 102-2, 102-3, and 102-N), via each of the corresponding multiple bottom stream outlets (120-1, 120-2, 120-3, and 120-N). In some embodiments, the multiple bottom stream outlets 120-1, 120-2, 120-3, and 120-N may be combined into a single bottom stream outlet 120 before entering the by-product pump 108. The flow rate of each of the multiple bottom stream outlets (120-1, 120-2, 120-3, and 120-N) is independently controlled. In the present embodiments, the by-product pump 108 is effective at driving the single bottom stream outlet 120, and is used to regulate the flow of the single bottom stream outlet 120 into the reboiler 110. In some embodiments, the by-product pump is in fluid communication with the reboiler 110 via a pumped liquid stream 122.

In the present disclosure, the reboiler 110 is a device that vaporizes the pumped liquid stream 122 again by raising the temperature of the pumped liquid stream 122 and evaporating. The reboiler 110 works as a heat exchanger which can exchange heat and has a vaporization space. The level of feed (e.g., the pumped liquid stream 122) in the reboiler 110 and the level of the reactive distillation columns (102-1, 102-2, 102-3, and 102-N) are, e.g., preferably at the same height. The pumped liquid stream 122 is preferably supplied from the bottom line into the reboiler 110. In some embodiments, about 10 to 50%, preferably 15 to 45%, preferably 20 to 40%, preferably 25 to 35%, or even more preferably 30% of the pumped liquid stream 122 is vaporized in the reboiler, resulting in a reboiler vapor stream (as represented by reference numeral 124), and a byproduct liquid stream (as represented by reference numeral 126), each % based on a total weight of the pumped liquid stream 122. In some embodiments, the reboiler vapor stream 124 is fed back to the reactive distillation columns (102-1, 102-2, 102-3, and 102-N), preferably to a feed inlet located in a lower section of one or more of the reactive distillation columns.

In some embodiments, the reboiler vapor stream 124 may be divided into multiple reboiler vapor stream inlets (124-1, 124-2, 124-3, and 124-N) before entering each of the corresponding reactive distillation column. The flow rate of each of the multiple reboiler vapor stream inlets (124-1, 124-2, 124-3, and 124-N) may be independently controlled. For example, the byproduct will be collected in a liquid form from the byproduct liquid stream 126, and the reboiler vapor stream 124 may be re-introduced into the reactive distillation columns. This second recirculating loop including the single bottom stream outlet 120, the pumped liquid stream 122, and the reboiler vapor stream 124, the by-product pump 108, the boiler 110, and the reactive distillation columns can be shared across multiple tanks that have different input and output requirements as a means of minimizing equipment size and cost.

Figure 3:
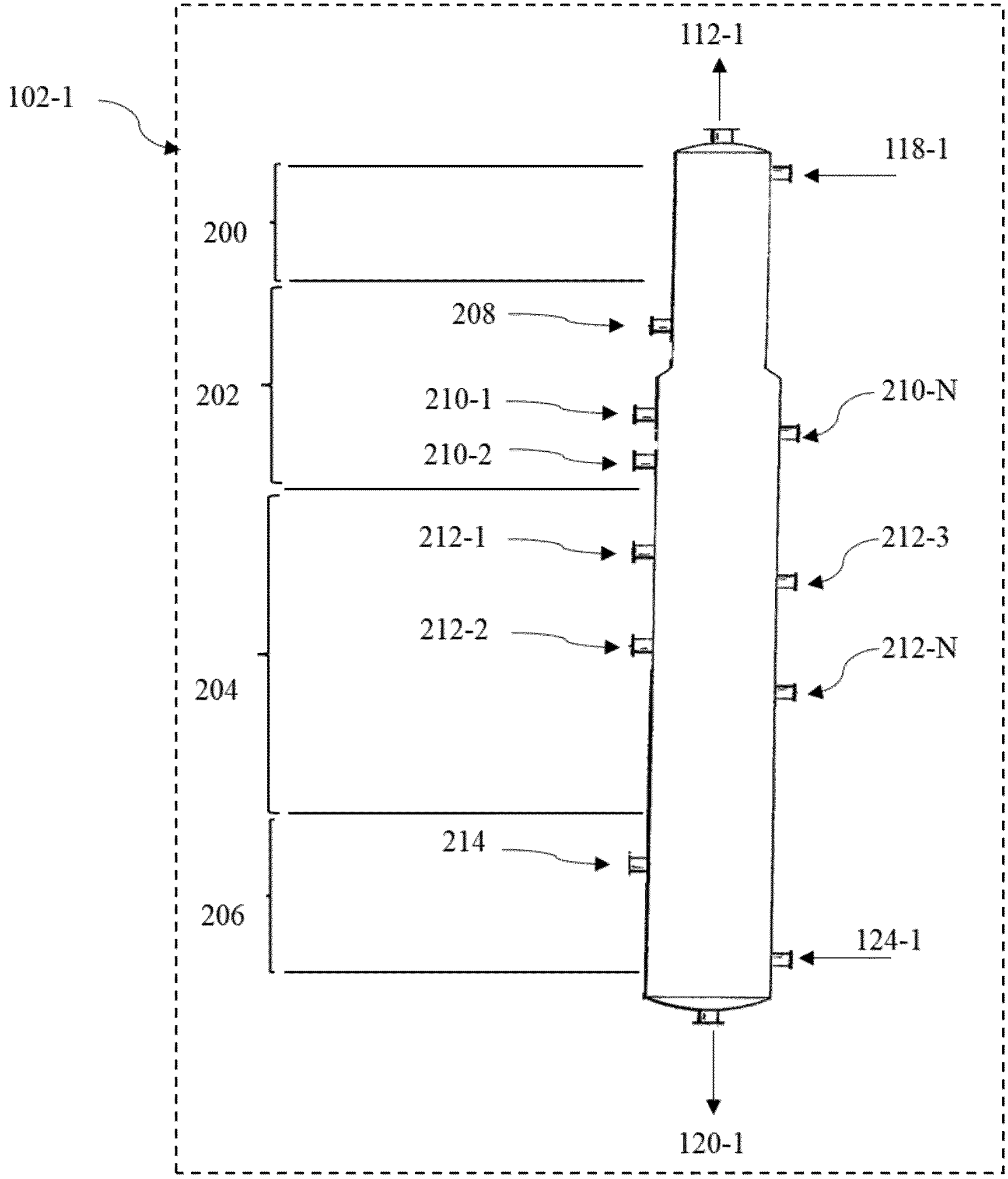
FIG. 3 is a schematic diagram of a reactive distillation column for use in the method of the present invention, according to certain embodiments.

Referring to FIG. 3, illustrated is a schematic diagram of a reactive distillation column for use in the method of the present invention, represented by reference numeral 102-1 and hereinafter sometimes referred to as "reactive distillation column" or "reactive distillation column 102-1" without any limitations. As illustrated, the reactive distillation column 102-1 is in the form of a vertical cylindrical vessel including an upper section, a body section (as represented by reference numeral 204), and a lower section (as represented by reference numeral 206). As used herein, the terms "length direction," or "longitudinal axis" generally refer to the vertical axis of the reactive distillation column in a vertical cylindrical shape. The upper section of the reactive distillation column 102-1 further includes a rectification section (as represented by reference numeral 200) and an extractive distillation section (as represented by reference numeral 202). In some embodiments, the rectification section 200 is in fluid communication with the body section 204 via the extractive distillation section 202. In some embodiments, the upper section is in fluid communication with the lower section 206 via the body section 204.

In some embodiments, the rectification section 200 of the reactive distillation column 102-1 includes a product stream outlet 112-1 at the uppermost portion of the rectification section 200. In some embodiments, the rectification section 200 further includes a reflux vapor stream inlet 118-1, located on an outer sidewall of the rectification section 200 of the reactive distillation column. In some embodiments, the product stream outlet 112-1 is in fluid communication with the refluxing unit 104.

In some embodiments, the extractive distillation section 202 of the reactive distillation column 102-1 includes a first reactant feed stream inlet (as represented by reference numeral 208), and a first plurality of catalyst feed stream inlets (as represented by reference numeral 210-1, 210-2, and 210-N). In some embodiments, acetic acid in the form of a liquid may be introduced to the extractive distillation 202 of the reactive distillation column 102-1 via the first reactant feed stream inlet 208. In some embodiments, at least a portion of the catalyst in the form of a liquid may be introduced into the reactive distillation column 102-1 via the first plurality of catalyst feed stream inlets 210-1, 210-2, and 210-N. In some embodiments, about 1 to 50%, preferably 5 to 45%, preferably 10 to 40%, preferably 15 to 35%, preferably 20 to 30%, or even more preferably about 25% of the catalyst in a liquid form may be introduced into the reactive distillation column 102-1, each % based on a total weight of the catalyst necessitated in order to catalyze the methyl acetate production. In some embodiments, the first plurality of catalyst feed stream inlets (210-1, 210-2, and 210-N) are evenly spaced apart and disposed along the length direction of the reactive distillation column 102-1, e.g., along the longitudinal axis at different heights. In some preferred embodiments, each of the first plurality of catalyst feed stream inlets (210-1, 210-2, and 210-N) are in different planes along the length direction of the reactive distillation column 102-1. In some more preferred embodiments, the first plurality of catalyst feed stream inlets (210-1, 210-2, and 210-N) are located on an outer sidewall of the extractive distillation section 202 of the reactive distillation column 102-1. In some most preferred embodiments, the level of the uppermost catalyst feed stream inlet 210-1 of the first plurality of catalyst feed stream inlets (210-1, 210-2, and 210-N) is under the level of the first reactant feed stream inlet 208. In some embodiments, N is a positive integer. In some preferred embodiments, N is 1 to 10, preferably 2 to 9, preferably 3 to 8, preferably 4 to 7, or even more preferably 5 to 6. Other ranges are also possible. In some most preferred embodiments, the flow rate of the catalyst introduced into the reactive distillation column 102-1 via each of the first plurality of catalyst feed stream inlets (210-1, 210-2, and 210-N) is independently controlled.

In some embodiments, the body section 204 of the reactive distillation column 102-1 includes a second plurality of catalyst feed stream inlets (as represented by reference numeral 212-1, 212-2, 212-3, and 212-N). In some embodiments, the second plurality of catalyst feed stream inlets (212-1, 212-2, 212-3, and 212-N) are evenly spaced apart and disposed along the length direction of the body section 204 of the reactive distillation column 102-1, along the longitudinal axis at different heights. In some embodiments, each of the second plurality of catalyst feed stream inlets (212-1, 212-2, 212-3, and 212-N) are at different heights along the length direction of the reactive distillation column 102-1. In some embodiments, the second plurality of catalyst feed stream inlets (212-1, 212-2, 212-3, and 212-N) are located on an outer sidewall of the body section 204 of the reactive distillation column 102-1. In some embodiments, the level of the uppermost catalyst feed stream inlet 212-1 of the second plurality of catalyst feed stream inlets (212-1, 212-2, 212-3, and 212-N) is under the level of the bottommost catalyst feed stream inlet 210-N of the first plurality of catalyst feed stream inlets (210-1, 210-2, and 210-N). In some embodiments, N is a positive integer. In some preferred embodiments, N is 1 to 10, preferably 2 to 9, preferably 3 to 8, preferably 4 to 7, or even more preferably 5 to 6. Other ranges are also possible. In some most preferred embodiments, the flow rate of the catalyst introduced into the reactive distillation column 102-1 via each of the second plurality of catalyst feed stream inlets (212-1, 212-2, 212-3, and 212-N) is independently controlled.

In some embodiments, the first plurality of catalyst feed stream inlets (210-1, 210-2, and 210-N), and the second plurality of catalyst feed stream inlets (212-1, 212-2, 212-3, and 212-N) are fluidly connected to the same catalyst feed stream, e.g., the first plurality of catalyst feed stream inlets and the second plurality of catalyst feed stream inlets are fluidly connected to a single liquid or gaseous feed stream. In some embodiments, the catalyst is introduced into the reactive distillation column 102-1 via at least two catalyst feed stream inlets. In some embodiments, each of the at least two catalyst feed stream inlets are independently selected from the group consisting of the first plurality of catalyst feed stream inlets (210-1, 210-2, and 210-N), and the second plurality of catalyst feed stream inlets (212-1, 212-2, 212-3, and 212-N). In some embodiments, each of the at least a portion of the catalyst are introduced at the same flow rate via the at least two catalyst feed stream inlets. In some further embodiments, each of the at least a portion of the catalyst are introduced at a different flow rate via the at least two catalyst feed stream inlets.

In some embodiments, the lower section 206 of the reactive distillation column 102-1 includes a second reactant feed stream inlet (as represented by reference numeral 214), a bottom stream outlet (as represented by reference numeral 120-1), and a reboiler vapor stream inlet (as represented by reference numeral 124-1). In some embodiments, the bottom stream outlet 120-1 is in fluid communication with a reboiler unit 110 via a by-product pump 108. In some embodiments, a reboiler vapor stream 124 is introduced into the reactive distillation columns (102-1, 102-2, 102-3, and 102-N) via the reboiler vapor stream inlets (124-1, 124-2, 124-3, and 124-N). In some embodiments, methanol in the form of a liquid may be introduced to the lower section 206 of the reactive distillation column 102-1 via the second reactant feed stream inlet 214. In some embodiments, the level of the second reactant feed stream inlet 214 is under the level of the bottommost catalyst feed stream inlet 212-N of the second plurality of catalyst feed stream inlets (212-1, 212-2, 212-3, and 212-N). In some embodiments, the level of the reboiler vapor stream inlet 124-1 is under the level of the second reactant feed stream inlet 214. In some embodiments, the bottom stream outlet 120-1 is at the bottommost point of the reactive distillation column 102-1.

Referring to FIG. 1, a flowchart depicting a method for making methyl acetate from methanol and acetic acid in the presence of a catalyst added portion wise is illustrated. The order in which the method 50 is described is not intended to be construed as a limitation, and any number of the described method steps may be combined in any order to implement the method 50. Additionally, individual steps may be removed or skipped from the method 50 without departing from the spirit and scope of the present disclosure.

At step 52, the method 50 includes simultaneously introducing the acetic acid in the form of a liquid to an upper section of a reactive distillation column 102-1 via a first reactant feed stream inlet 208 and the methanol in the form of a vapor to a lower section 206 of the reactive distillation column 102-1 via a second reactant feed stream inlet 214. In some embodiments, the acetic acid and methanol are introduced to the reactive distillation column 102-1 in approximately stoichiometric quantities. In some embodiments, the acetic acid and methanol will be fed in a molar ratio of about 2:1 to 1:2, or even more preferably about 1:1. Other ranges are also possible. In the present disclosure, the term "approximately stoichiometric quantities" generally refers to the methanol is added in slight excess, e.g., about 3% more, about 5% more, about 10% more, or even more preferably about 20% more, each % based on a total moles of the acetic acid. In some embodiments, an excess amount of methanol may be removed from the bottom stream outlet 120-1 of the reactive distillation column 102-1 with the waste water and can be reintroduced to the second reactant feed stream inlet 214 following purification.

In some embodiments, the methanol fed into the reactive distillation column 102-1 via the second reactant feed stream inlet 214 may contain no more than 20% water, preferably no more than 10% water, preferably no more than 5% water, or even more preferably no more than 1% water by weight. Other ranges are also possible. The incorporation of a water-containing methanol into the method of the present invention exhibits no adverse effect on the operation of the reactive distillation system and the reactive distillation column 102-1.

In some embodiments, the acetic acid fed into the reactive distillation column 102-1 via the first reactant feed stream inlet 208 may contain no more than 20% impurity, preferably no more than 10% impurity, preferably no more than 5% impurity, or even more preferably no more than 1% impurity by weight. Other ranges are also possible. In some embodiments, the impurity contains at least one selected from the group consisting of ethyl acetate, propionic acid, n-propyl acetate, and water. The incorporation of an impurity-containing acetic acid into the method of the present invention exhibits no adverse effect on the operation of the reactive distillation system and the reactive distillation column 102-1.

In some embodiments, the upper section of the reactive distillation column 102-1 includes a rectification section 200 and an extractive distillation section 202. The rectification section contains a product stream outlet 112-1 and a reflux vapor stream inlet 118-1. The extractive distillation section includes the first reactant feed stream inlet 208, and a first plurality of catalyst feed stream inlets (210-1, 210-2, and 210-N).

In some embodiments, the reactive distillation column 102-1 is in the form of a vertical cylindrical vessel containing the upper section, the lower section 206, and a body section 204 between the upper section and the lower section 206. The upper section is continuous with and is in fluid communication with the lower section 206 via the body section 204.

In some embodiments, the body section 204 of the reactive distillation column 102-1 includes a second plurality of catalyst feed stream inlets (212-1, 212-2, 212-3, and 212-N).

In some embodiments, the lower section 206 of the reactive distillation column 102-1 includes the second reactant feed stream inlet 214, a bottom stream outlet 120-1, and a reboiler vapor stream inlet 124-1.

At step 54, the method 50 includes contacting the acetic acid and the methanol in countercurrent flow in the body section 204 of the reactive distillation column 102-1, and introducing at least a portion of the catalyst in the form of a liquid via at least two catalyst feed stream inlets thereby reacting the acetic acid and the methanol in the presence of the catalyst to form the methyl acetate in the form of a vapor and water.

In one embodiment, methanol and acetic acid are reacted in a single continuous reactive distillation column 102-1. In a preferred embodiment, the method 50 of the present disclosure provides sufficient residence time to achieve high conversion of the reactants to high purity methyl acetate product. As used herein, the term "high reactant conversion" generally refers to a conversion of at least about 98%, or even more preferably about 99%. For example, in the method of the present invention, a conversion of acetic acid of about 98%, preferably about 99% and a conversion of methyl alcohol of 98%, preferably about 99.5% are achieved. Unless otherwise specified, all percentages used herein are weight percentages.

In one embodiment, as methyl acetate is formed from methanol and acetic acid, the method 50 also leads to the concurrent generation of azeotropes. Specifically, two azeotropes may be produced, including a first azeotrope of methyl acetate and water which contains approximately 3 to 8%, or even more preferably about 5% by weight of water in methyl acetate, and the second azeotrope of methanol and methyl acetate which contains around 15 to 25%, or even more preferably about 20% by weight of methanol in methyl acetate. Other ranges are also possible. In some embodiments, the enhanced product purity mentioned above is attained by utilizing acetic acid as the extractive agent, which effectively breaks the azeotropes between methyl acetate and water, as well as between methyl acetate and methanol. In some embodiments, the method 50 for removing methanol from the methyl acetate/methanol azeotrope involves its reaction with acetic acid.

In some embodiments, the catalyst is at least one acid selected from the group consisting of sulfuric acid, phosphoric acid, hydrochloric acid, p-toluenesulfonic acid, and methanesulfonic acid. In some preferred embodiments, the catalyst is sulfuric acid. In some more preferred embodiments, the sulfuric acid is in the form of a solution having a concentration of 20 to 99.9 wt. %, preferably 40 to 99.5 wt. %, preferably 60 to 99 wt. %, preferably 80 to 98.5 wt. %, preferably 95 to 98 wt. %, or even more preferably about 98 wt. %, each wt. % based on a total weight of the sulfuric acid solution. Other ranges are also possible.

In some embodiments, the catalyst may further include an acidic cation exchange resin. The acid cation exchange resin may be preloaded and supported on a plurality of trays located within the reactive distillation column 102-1. The acidic cation exchange resin includes at least one of a weak acid cation exchange resin, a strong acid cation exchange resin, and/or combinations thereof. In one embodiment, the acidic cation exchange resin is a strong acid cation exchange resin having a polystyrene matrix and a sulfonic acid functional group. In a further embodiment, the strong acid cation exchange resin may have a sulfonic acid functional group polystyrene, sulfonic acid functional group polystyrene, and mixtures thereof. As used herein, the term "strong acid cation exchange resin" generally refers to a resin with functional groups that are typically strong acids with pKa less than 1.

In another embodiment, the acidic cation exchange resin is a weak acid exchange resin having a polyacrylic copolymer matrix and a carboxylic acid functional group. Preferably, the weak acid exchange resin has a surface with functional groups containing carboxylic acids. Alternatively, the ion exchange resin has a surface containing sulfonic acids functional groups. As used herein, the term "weak acid exchange resin" generally refers to a resin with functional groups that are typically weak acids with pKa greater than 1. Typical weakly acidic functional groups include carboxylic acid, chlorocarboxylic acid, and phosphonic acid groups.

In a specific embodiment the reactive distillation column 102-1 may further include a housing having an open top, and open bottom supportably maintained with the body section 204 of the reactive distillation column 102-1. In a preferred embodiment, the housing is located at the intersection of the extractive distillation section 202 and the body section 204. In a more preferred embodiment, the housing is located at the uppermost portion of the body section 204, and below the extractive distillation section 202. In some embodiments, when the catalyst is the acidic cation exchange resin in a solid form, the catalyst material is supportably retained within the housing permitting fluid flow therethrough.

In some embodiments, the housing retaining particles of the catalyst is in a packed bed configuration. The catalyst is tightly packed inside the housing, creating a uniform and dense column containing the catalyst particles. In a preferred embodiment, the fluid flows through the spaces between the catalyst particles, contacting the surface of the catalyst and undergoing the esterification of methanol and acetic acid.

In some embodiments, the housing retaining particles of the catalyst may further contain perforated plates and/or grids that are evenly stacked or spaced at intervals within the body section 204. In a preferred embodiment, the plates and/or grids have holes or openings that permit the fluid to pass through while keeping the catalyst particles contained.

In some embodiments, the housing retaining particles of the catalyst may further contain one or more fixed support structures selected from the group consisting of a rod, a baffle, and a shelve, that help retain the catalyst particles in the housing.

In some embodiments, the housing retaining particles of the catalyst may be in a monolithic structure having a plurality of intricate internal channels and a plurality of pores. In some other embodiments, the housing retaining particles of the catalyst may be in a honeycomb-like structure having a network of interconnected channels and cells.

In some embodiments, the methanol flows axially from the second reactant feed stream inlet 214 to the opening bottom of the housing, and simultaneously contacting with the acetic acid that flows axially from the first reactant feed stream inlet 208 to the opening top of the housing.

In some embodiments, the catalyst is provided to the reactive distillation system and reactive distillation column 102-1 in a concentration sufficient to provide the desired catalytic effect. In some embodiments, when sulfuric acid is used as the catalyst, the flow rate is about one kg of sulfuric acid per 50 to 200 kg of acetic acid feed, preferably 75 to 180 kg, preferably 100 to 160 kg, or even more preferably 120 to 140 kg of acetic acid feed. Other ranges are also possible. In some preferred embodiments, when sulfuric acid is used as the catalyst, a portion of the catalyst in the form of a liquid introduced via the at least two catalyst feed stream inlets is no more than one third of the combined amount of the catalyst required to catalyze the esterification of methanol and acetic acid, preferably no more than one fourth, preferably no more than one fifth, or even more preferably no more than one tenth of the combined amount of the catalyst, e.g., varying aliquots of acid are added independently through different inlets and/or the total flow of catalyst is added in divided streams. Other ranges are also possible.

In some preferred embodiments, the methanol and the acetic acid react in the presence of the catalyst, at an uppermost point of the body section 204 of the reactive distillation column 102-1, to form the methyl acetate at a temperature $T_1$. In some embodiments, temperatures in the body section 204 below the uppermost point of the body section 204 are higher than $T_1$. In some embodiments, a temperature in the lower section 206 is higher than $T_1$. In some further embodiments, a temperature in the upper section of the reactive distillation column 102-1 above the uppermost point of the body section 204 is less than $T_1$.

Figure 5:
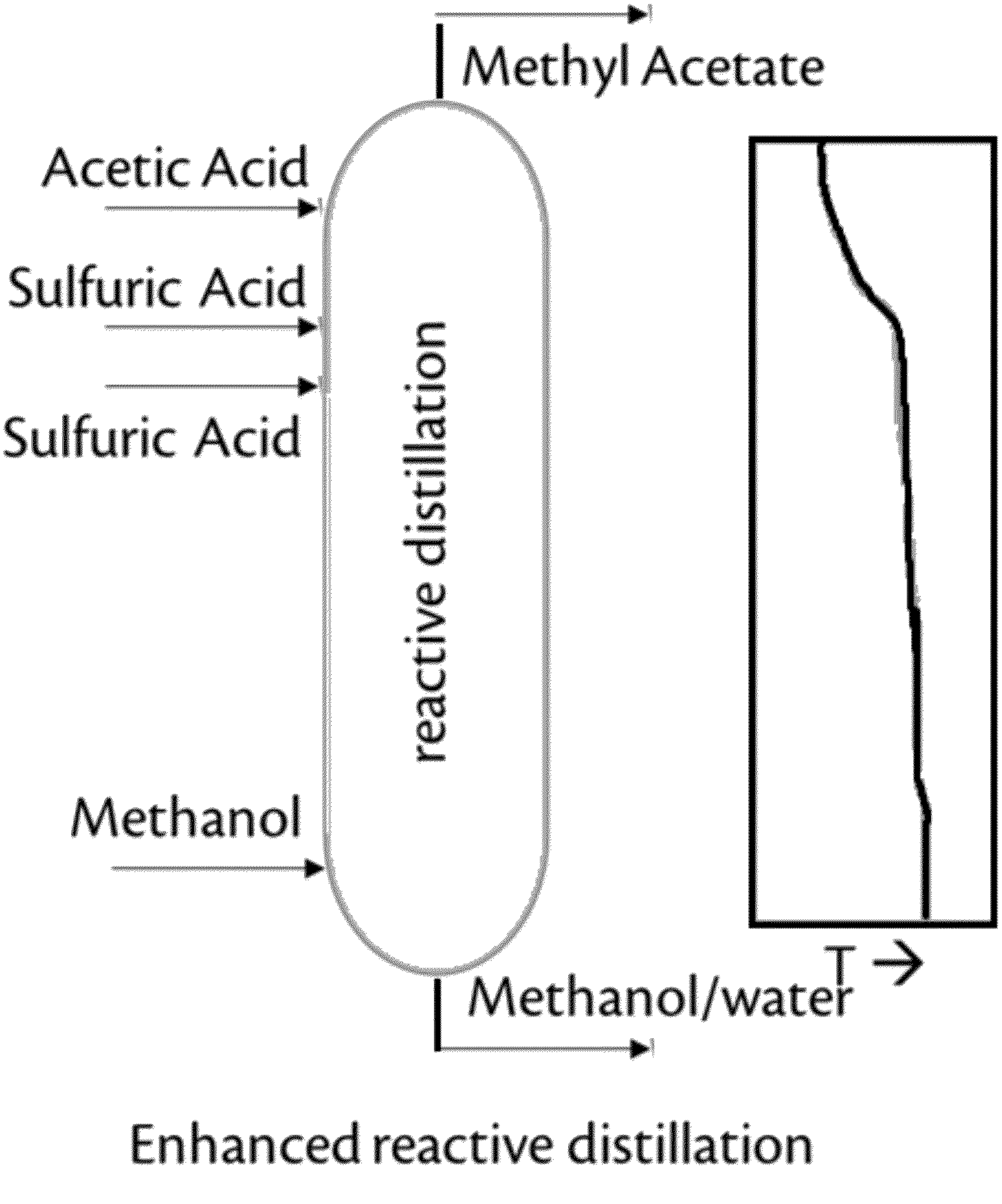
FIG. 5 shows a temperature profile of the reactive distillation column for use in the method of making methyl acetate from methanol and acetic acid in the presence of a catalyst added portion wise at multiple catalyst feed stream inlets, according to certain embodiments.

Referring to FIG. 5, illustrated is a temperature profile of the reactive distillation column for use in the method of making methyl acetate from methanol and acetic acid in the presence of an acid catalyst added portion wise at multiple catalyst feed stream inlets. In some embodiments, a temperature in the body section 204 of the reactive distillation column 102-1 from the uppermost point of the body section 204 to a bottommost portion of the body section 204 is within the range of $T_1$ to $T_1$+30° C., preferably Tito $T_1$+20° C., preferably $T_1$ to $T_1$+10° C., or even more preferably $T_1$ to $T_1$+5° C. Other ranges are also possible. In some embodiments, a temperature in the upper section of the reactive distillation column 102-1 is about 50° C. lower, preferably about 30° C. lower, preferably about 10° C. lower, or even more preferably about 5° C. lower than the uppermost point of the body section 204 of the reactive distillation column 102-1. Other ranges are also possible. In some further preferred embodiments, the catalyst is introduced portion wise via each of the at least two catalyst feed stream inlets as the reaction progresses over time, resulting in a flattened temperature profile of the reaction of making methyl acetate from acetic acid and methanol, as depicted in FIG. 5. In some embodiments, no bumps or deviations more than 3° C., preferably more than 5° C., or even more preferably more than 10° C. around a mean temperature within the body section 204 of the reactive distillation column 102-1 is observed during the method of making methyl acetate. Other ranges are also possible.

Figure 4:
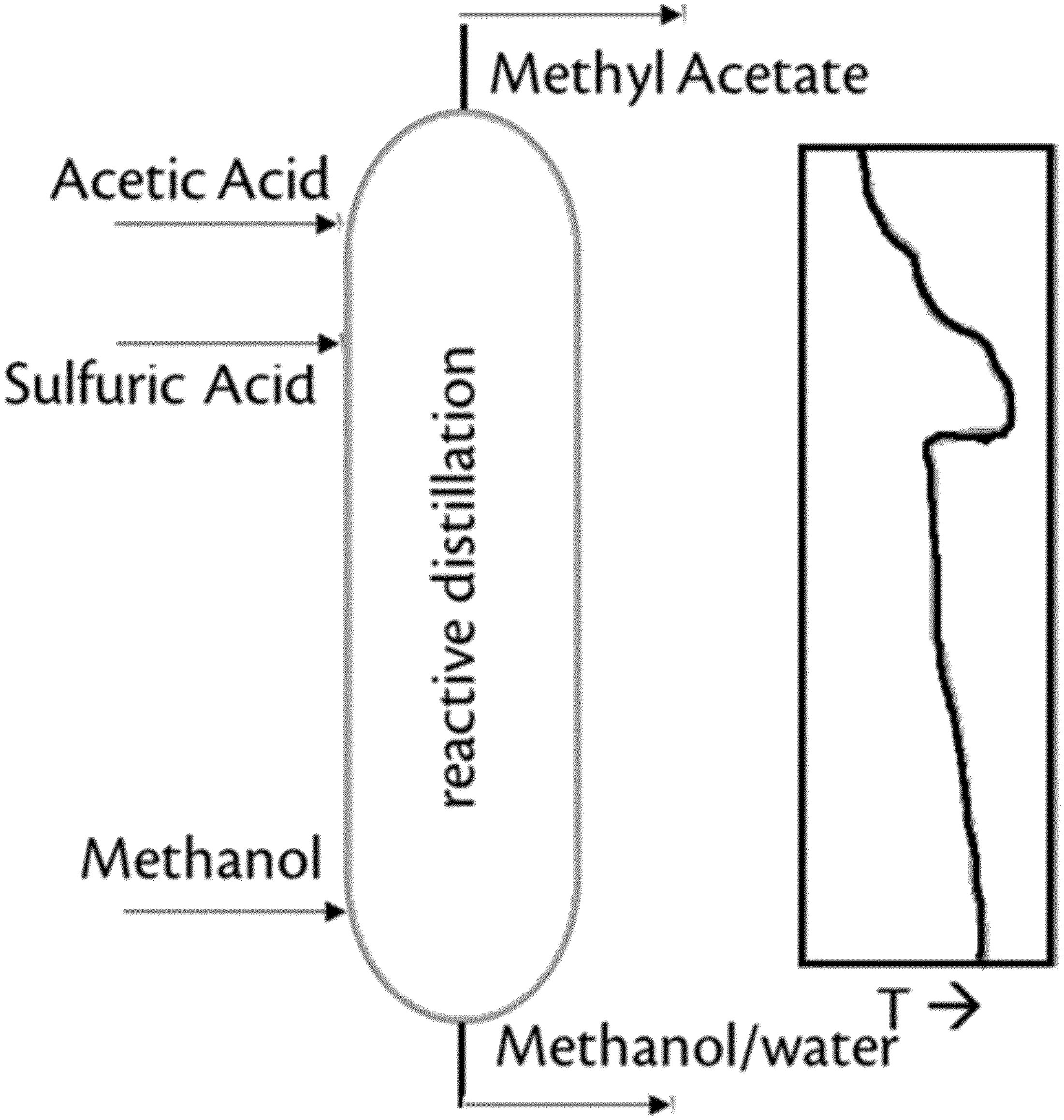
FIG. 4 shows a temperature profile of a reactive distillation column for use in a method of making methyl acetate from methanol and acetic acid with the catalyst added at a single catalyst feed stream inlet, according to certain embodiments.

Referring to FIG. 4, illustrated a temperature profile of a reactive distillation column for use in a method of making methyl acetate from methanol and acetic acid with the catalyst added at a single catalyst feed stream inlet. In some embodiments, temperatures in the body section of the reactive distillation column from an uppermost portion are lower than temperatures from a middle and bottommost portion of the body section of the same reactive distillation column. In some embodiments, the temperatures of the uppermost portion are at least 5° C. lower, preferably 10° C. lower, preferably 20° C. lower, preferably 30° C. lower, preferably 40° C. lower, or even more preferably 50° C. lower, than the middle and bottommost portion of the body section of the reactive distillation column. In some further embodiments, the catalyst is introduced via a single catalyst feed stream inlet, resulting in an unsmoothed temperature profile of the reaction of making methyl acetate from acetic acid and methanol, as depicted in FIG. 4.

In some embodiments, the reactive distillation column 102-1 may be operated at a temperature in the body section 204 of about 50 to 120° C., preferably 60 to 100° C., or even more preferably 70 to 80° C. Other ranges are also possible. In some other embodiments, the temperature may be less than 50° C. or higher than 120° C., dependent upon the number of the reactive distillation columns in the reactive distillation system, the target production rate, the operating pressure, the corrosion rates which can be tolerated by the apparatus. Typically, it is desirable to maintain as low a temperature as possible for a given production rate, and it can be determined by one of ordinary skill in the art using suitable known methods.

In some embodiments, the reactive distillation column 102-1 may be operated at a pressure in the body section 204 of about 0.9 to 4 atmospheres, preferably 1 to 2 atmospheres, or even more preferably about 1.1 to 1.5 atmospheres. Other ranges are also possible. Typically, it is desirable to maintain as low a pressure as possible for a given production rate, and it can be determined by one of ordinary skill in the art using suitable known methods.

In some embodiments, the reactive distillation system of the present disclosure has a residence time of about 1 to 12 hours, preferably about 1.5 to 10 hours, preferably about 2 to 8 hours, preferably about 2.5 to 6 hours, or even more preferably about 3 to 4 hours. Other ranges are also possible. As used herein, the term "residence time" generally refers to the clear liquid hold-up volume in the reaction trays divided by the sum of the volumetric flow rates of acetic acid and methanol. Typically, it is desirable to maintain a residence time above the minimum residence time for a given production rate, and it can be determined by one of ordinary skill in the art using suitable known methods. In a preferred embodiment, the high hold-up times required to attain the minimum residence time in the present process is achieved through the use in the reaction section of reverse flow trays having high weirs, high bubble cap risers, and large inlet and flow reversing zone sumps.

In some preferred embodiments, the reactive distillation system of the present disclosure has a reflux ratio of about 0.5 to 5, preferably 0.8 to 4, preferably 1.1 to 3, or even more preferably about 1.4 to 2. Other ranges are also possible. As used herein, the term "reflux ratio" generally refers to the ratio of the overhead reflux flow rate to the overhead product flow rate. In a preferred embodiment, it is desirable to maintain a reflux ratio above the minimum reflux ratio for a given production rate, and it can be determined by one of ordinary skill in the art using suitable known methods.

In some embodiments, turbine meters may be operatively configured to the first reactant feed stream inlet 208, the second reactant feed stream inlet 214, and the product stream outlet 112-1 to measure the flows of acetic acid, methanol, and methyl acetate respectively. The incorporation of the turbine meter to the reactive distillation system allows the material balance of the process to be checked to ensure proper control of the process. In some further embodiments, orifice meters may be operatively configured to the first plurality of catalyst feed stream inlets (e.g., 210-1, 210-2, and 210-N), the second plurality of catalyst feed stream inlets (e.g., 212-1, 212-2, and 210-N), and the bottom stream outlet 120-1 to measure the reflux flow rate, the sulfuric acid flow rate, and the steam flow to the bottom of the reactive distillation column. A back-up meter is provided in case the sulfuric acid orifice meter fails.

In some preferred embodiments, a continuous in-line water analyzer, calibrated for 0-10,000 ppm water in methyl acetate, can be operatively configured to the product stream outlet 112-1. This incorporation of the in-line water analyzer ensures a smooth operation of the process and the assurance of high quality product.

In some more preferred embodiments, the reactive distillation column 102-1 may have approximately 10 to 100 trays, preferably 30 to 80 trays, or even more preferably 50 to 60 trays in the body section 204. These trays are preferably of the bubble cap type. In some more preferred embodiments, the reactive distillation column 102-1 may have approximately 1 to 20 trays, preferably 5 to 15 trays, or even more preferably about 10 trays for the rectification section 200. In some even more preferred embodiments, the reactive distillation column 102-1 may have approximately 1 to 20 trays, preferably 5 to 15 trays, or even more preferably about 10 trays for the extractive distillation section 202. In some most preferred embodiments, the reactive distillation column 102-1 may have approximately 1 to 20 trays, preferably 5 to 15 trays, or even more preferably about 10 trays for the lower section 206. Other ranges are also possible.

In some embodiments, the total number of trays in the reactive distillation column 102-1 is at least 10 more, preferably at least 20 more, or even more preferably at least 30 more than the total number of trays in a next reactive distillation column 102-2. In some further embodiments, the total number of trays in the reactive distillation column 102-2 is at least 5 more, preferably at least 10 more, or even more preferably at least 15 more than the total number of trays in a next reactive distillation column 102-3. In some preferred embodiments, the total number of trays in the reactive distillation column 102-3 is substantially the same as the total number of trays in a next reactive distillation column 102-N. In some more preferred embodiments, each of the reactive distillation columns 102-1, 102-2, 102-3, and 102-N, has substantially the same total number of trays, respectively. Other ranges are also possible As used herein, the term "tray" generally refers to a horizontal or angled plate or stage that is used to facilitate the chemical reactions occurring simultaneously within the column. In the present disclosure, the "tray" may provide the hold-up times which are preferred in the process of the present invention. The high hold-up times may further be achieved through the use of reverse flow trays that have high weirs, high bubble cap risers, and large inlet and flow reversing zone sumps.

In some embodiments, the tray described in the present disclosure is at least one type of tray selected from the group consisting of a sieve tray, a valve tray, a crossflow valve tray, a bubble cap tray, a fixed valves tray, a dual-flow tray, a structured packing tray, a perforated plate tray, and a wire mesh tray. In some further embodiments, each of the reactive distillation columns 102-1, 102-2, 102-3, and 102-N, has at least two types of trays, preferably at least three types of trays, or even more preferably at least four types of trays selected from the group consisting of a sieve tray, a valve tray, a crossflow valve tray, a bubble cap tray, a fixed valves tray, a dual-flow tray, a structured packing tray, a perforated plate tray, and a wire mesh tray. In some preferred embodiments, each section within the same reactive distillation column, e.g., 102-1, has the same type of tray. In some embodiments, the rectification section 200 of the reactive distillation column 102-1 contains 10 to 15, preferably about 12 crossflow valve trays spaced 10 to 50, or even more preferably 15 to 20 inches apart. In some embodiments, the extractive distillation section 202 of the reactive distillation column 102-1 contains 10 to 15, preferably about 12 crossflow valve trays spaced 10 to 50, or even more preferably 15 to 20 inches apart. In some embodiments, the body section 204 of the reactive distillation column 102-1 contains 40 to 80, preferably about 50 to 60 reverse flow bubble cap trays spaced 10 to 50, or even more preferably 20 to 30 inches apart. In some embodiments, the lower section 206 of the reactive distillation column 102-1 contains 10 to 15, preferably about 12 reverse flow valve trays spaced 10 to 50, or even more preferably 15 to 20 inches apart. Other ranges are also possible.

At step 56, the method 50 includes removing the methyl acetate from the upper section of the reactive distillation column via the product stream outlet 112-1, and removing water and an excess amount of methanol from the bottom stream outlet 120-1. In some embodiments, the product stream outlet 112-1 containing the methyl acetate is introduced into the refluxing unit 104 for further purification. In some embodiments, the methyl acetate is separated from the product stream and collected in a storage tank unit 106.

In some embodiments, the removing the methyl acetate also involves the removal of acetic acid, and other azeotropes that have substantially similar boiling points as methyl acetate. A vapor containing the methyl acetate is withdrawn from the product stream outlet 112-1, and passed through a wire mesh separator which removes any entrained gaseous catalyst, such as sulfuric acid, which is returned to the reactive distillation column 102-1. The vapor containing the methyl acetate is then fed to a reflux unit 104 where methyl acetate is separated from its azeotropes. A reflux vapor steam 118 may be then fed to a reactive distillation column selected from the group consisting of 102-2, 102-3, and 102-N. In some embodiments, the reflux vapor steam 118 may be returned to the first reactive distillation column 102-1.

In some embodiments, the method of the present invention also includes the use of a methyl acetate storage tank 106. The storage tank 106 is preferably located between the body section 204 and the reboiler 110 of the reactive distillation system. In some embodiments, the location and size of the storage tank 106 may vary.

In some embodiments, the water and an excess amount of methanol removed from the bottom stream outlet 120-1 of the reactive distillation column 102-1 may be passed through a by-product pump and a reboiler sequentially to form a reboiler vapor stream 124. In some preferred embodiments, the reboiler vapor stream 124 may be returned to a reactive distillation column selected from the group consisting of 102-2, 102-3, and 102-N. In some more preferred embodiments, the reboiler vapor stream 124 may be returned to the reactive distillation column 102-1.

In some embodiments, the methyl acetate formed by contacting the acetic acid and the methanol has a purity of at least about 95%, preferably at least about 96%, preferably at least about 97%, preferably at least about 98%, preferably at least about 99%, or even more preferably at least about 99.9% by weight pure, as determined by gas chromatography (GC). In some embodiments, the methyl acetate has a moisture content of less than 0.5%, preferably less than 0.1%, preferably less than 0.05%, or even more preferably less than 0.01% by weight, as determined by coulometry. In some embodiments, the methyl acetate has a residue content of less than 0.01%, preferably less than 0.005%, preferably less than 0.001%, or even more preferably less than 0.0005% by weight, as determined by an evaporation method. Other ranges are also possible.

In some embodiments, a combined amount of the catalyst introduced portion wise is no more than an amount of the catalyst required in a method of making a same amount of methyl acetate from methanol and acetic acid with the catalyst added at a single catalyst feed stream inlet. In some embodiments, the combined amount of the catalyst introduced portion wise is 5% less, preferably 10% less, preferably 20% less, or even more preferably 30% less by weight than the amount of the catalyst required in the method of making the same amount of methyl acetate from methanol and acetic acid with the catalyst added at a single catalyst feed stream inlet.

In some embodiments, the method of making methyl acetate from methanol and acetic acid in the presence of a catalyst added portion wise has a production rate increased by 10 to 50%, preferably 15 to 40%, or even more preferably 20 to 30% compared to a method of making methyl acetate from methanol and acetic acid with the catalyst added at a single catalyst feed stream inlet in a system of otherwise equivalent or equal dimensions and structure.

The above description demonstrates a method for making methyl acetate from methanol and acetic acid in the presence of a catalyst added portion wise, as described herein. The description and corresponding examples are provided for illustration and are not to be construed as limitations of the present disclosure, as many variations thereof are possible without departing from the spirit and scope of the present disclosure.

The present invention provides a method for the reaction of methanol and acetic acid using a reactive distillation system containing one or more reactive distillation columns. The temperature profile of the present disclosure shows a flattened temperature profile as the reaction rate is proportional to catalyst concentration. This reduced temperature bump in the column results in less corrosion. Additionally, the multi point catalyst feeding increased the reaction zone length, as well as the reactor volume, which results in enhanced production rate of methyl acetate.

Numerous modifications and variations of the present disclosure are possible in light of the above teachings. It is therefore to be understood that within the scope of the appended claims, the invention may be practiced otherwise than as specifically described herein.

The invention claimed is:

1. A method for making methyl acetate from methanol and acetic acid in the presence of a catalyst added portion wise, the method comprising:

simultaneously introducing the acetic acid in the form of a liquid to an upper section of a reactive distillation column via a first reactant feed stream inlet and the methanol in the form of a vapor to a lower section of the reactive distillation column via a second reactant feed stream inlet;

wherein the reactive distillation column is in the form of a vertical cylindrical vessel comprising the upper section, the lower section, and a body section between the upper section and the lower section, wherein the upper section is continuous with and in fluid communication with the lower section via the body section;

wherein the upper section of the reactive distillation column comprises a rectification section and an extractive distillation section, wherein the rectification section comprises a product stream outlet, and wherein the extractive distillation section comprises the first reactant feed stream inlet, and a first plurality of catalyst feed stream inlets;

wherein the body section of the reactive distillation column comprises a second plurality of catalyst feed stream inlets;

wherein the lower section of the reactive distillation column comprises the second reactant feed stream inlet, a bottom stream outlet, and a reboiler vapor stream inlet;

contacting the acetic acid and the methanol in counter-current flow in the body section of the reactive distillation column, and introducing at least a portion of the catalyst in the form of a liquid via at least two catalyst feed stream inlets thereby reacting the acetic acid and the methanol in the presence of the catalyst to form the methyl acetate in the form of a vapor and water;

removing the methyl acetate from the upper section of the reactive distillation column via the product stream outlet, and removing water and an excess amount of methanol from the bottom stream outlet.

2. The method of claim 1, wherein the catalyst is at least one acid selected from the group consisting of sulfuric acid, phosphoric acid, hydrochloric acid, p-toluenesulfonic acid, and methanesulfonic acid.

3. The method of claim 2, wherein the catalyst is sulfuric acid.

4. The method of claim 1, wherein the product stream outlet is in fluid communication with a refluxing unit.

5. The method of claim 1, wherein the bottom stream outlet is in fluid communication with a boiler unit via a by-product pump, and wherein a reboiler vapor stream is introduced into the reactive distillation column via the reboiler vapor stream inlet.

6. The method of claim 1, wherein the first plurality of catalyst feed stream inlets are evenly spaced apart and disposed along the length direction of the reactive distillation column.

7. The method of claim 1, wherein each of the first plurality of catalyst feed stream inlets are in different planes along the length direction of the reactive distillation column.

8. The method of claim 1, wherein the first plurality of catalyst feed stream inlets are located on an outer sidewall of the extractive distillation section of the reactive distillation column.

9. The method of claim 1, wherein the second plurality of catalyst feed stream inlets are evenly spaced apart and disposed along the length direction of the body section.

10. The method of claim 1, wherein each of the second plurality of catalyst feed stream inlets are in different planes along the length direction of the reactive distillation column.

11. The method of claim 1, wherein the second plurality of catalyst feed stream inlets are located on an outer sidewall of the body section of the reactive distillation column.

12. The method of claim 1, wherein the first and second plurality of catalyst feed stream inlets are fluidly connected to the same catalyst feed stream.

13. The method of claim 1, wherein each of the at least two catalyst feed stream inlets are independently selected from the group consisting of the first plurality of catalyst feed stream inlets and the second plurality of catalyst feed stream inlets.

14. The method of claim 1, wherein each of the at least a portion of the catalyst are introduced at the same flow rate via the at least two catalyst feed stream inlets.

15. The method of claim 1, wherein the methanol and the acetic acid react in the presence of the catalyst, at an uppermost point of the body section of the reactive distillation column, to form the methyl acetate at a temperature $T_1$, wherein temperatures in the body section below the uppermost point of the reactive distillation column are higher than $T_1$ and a temperature in the lower section is higher than $T_1$.

16. The method of claim 15, wherein a temperature in the body section of the reactive distillation column from the uppermost point of the body section to a bottommost portion of the body section is within the range of $T_1$ to $T_1$+30° C.

17. The method of claim 1, wherein the catalyst is introduced portion wise via each of the at least two catalyst feed stream inlets as the reaction progresses over time, resulting in a flattened temperature profile of the reaction of making methyl acetate from acetic acid and methanol.

18. The method of claim 1, wherein a combined amount of the catalyst introduced portion wise is no more than an amount of the catalyst required in a method of making a same amount of methyl acetate from methanol and acetic acid with the catalyst added at a single catalyst feed stream inlet.

19. The method of claim 1, having a production rate increased by 20 to 30% compared to a method of making methyl acetate from methanol and acetic acid with the catalyst added at a single catalyst feed stream inlet.

20. The method of claim 1, wherein the methyl acetate formed by contacting the acetic acid and the methanol is at least about 95% pure determined by gas chromatography (GC).

* * * * *